(12) United States Patent
Dishler

(10) Patent No.: US 11,642,246 B1
(45) Date of Patent: *May 9, 2023

(54) VIBRATING SURGICAL INSTRUMENT

(71) Applicant: Jon Gordon Dishler, Greenwood Village, CO (US)

(72) Inventor: Jon Gordon Dishler, Cherry Hills Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,571

(22) Filed: Dec. 6, 2021

(51) Int. Cl.
*A61F 9/013* (2006.01)
*A61B 90/00* (2016.01)
*A61B 17/00* (2006.01)
*A61B 17/32* (2006.01)

(52) U.S. Cl.
CPC .. *A61F 9/0133* (2013.01); *A61B 2017/00017* (2013.01); *A61B 2017/320044* (2013.01); *A61B 2017/320078* (2017.08); *A61B 2017/320082* (2017.08); *A61B 2090/0817* (2016.02)

(58) Field of Classification Search
CPC ............. A61F 9/013; A61F 9/0133; A61F 9/00745–00763; A61F 9/007–0136; A61B 2017/320082; A61B 2017/320078; A61B 2017/320044; A61B 2017/00017; A61B 2090/0817; A61B 17/32–326;
(Continued)

(56) References Cited

U.S. PATENT DOCUMENTS 3,526,219 A * 9/1970 Lewis ............ A61B 17/320068
433/91
3,942,519 A 3/1976 Shock
4,570,632 A 2/1986 Woods
(Continued)

FOREIGN PATENT DOCUMENTS

JP 2020188905 A 11/2020
KR 200309779 Y1 4/2003

OTHER PUBLICATIONS

Datasheet, DA7282, LRA/ERM Ultra-Low Haptic Driver with Multiple Input Triggers and Integrated Waveform Memory, Jul. 30, 2019, 77 pgs., Dialog Semiconductor CFR0011-120-00.
Sinha, Rahesh MD, et al., Ophthalmic Surgical Instruments, First Edition, 2017, 40 pgs, Jaypee Brothers Medical Publishers Ltd.
Wikipedia contributors, "Refractive Surgery", The Free Encyclopedia, Wikipedia, retrieved from https://en.wikipedia.org/wiki/Refractive_surgery on Oct. 12, 2021.
(Continued)

*Primary Examiner* — Darwin P Erezo
*Assistant Examiner* — Brigid K Byrd
(74) *Attorney, Agent, or Firm* — Ungerman IP PLLC; Mark E Ungerman

(57) ABSTRACT

A vibrating tissue separator suitable for use in separating a lenticule established by a femtosecond laser during a smile procedure may include a surgical implement such as a blunt spatula mounted on a handle that carries a haptic actuator for applying vibratory motion to the surgical implement. A damping arrangement may be provided to isolate the surgeons hand from the vibrations which would otherwise be transmitted through the handle. The actuator may apply a linear vibration along the axis of the handle which applies a lifting and chopping motion to the tip of a surgical implement having a bend. The tip may be suitable to the tissue being separated. For example, for SMILE lenticule separation, a blunt or semi-sharp spatula, blunted wire or loop may be used. The direction of vibration at the tip may be changed by rotating the implement in a plane other than the plane of the bend or by rotating an actuator such as an LRA with respect to the handle.

22 Claims, 7 Drawing Sheets

(58) Field of Classification Search
CPC ........... A61B 17/320068–2017/320098; A61C 1/06–07
See application file for complete search history.

(56) References Cited

U.S. PATENT DOCUMENTS

| | | | |
|---|---|---|---|
| 4,637,393 A * | 1/1987 | Ray | A61F 9/0133 606/166 |
| 4,674,503 A * | 6/1987 | Peyman | B26D 7/2628 83/881 |
| 4,911,161 A | 3/1990 | Schechter | |
| 5,047,008 A | 9/1991 | Juan, Jr. et al. | |
| 5,112,339 A | 5/1992 | Zelman | |
| 5,154,694 A | 10/1992 | Kelman | |
| 5,180,363 A | 1/1993 | Idemoto et al. | |
| 5,222,960 A | 6/1993 | Poley | |
| 5,258,002 A * | 11/1993 | Jeffers | A61B 17/3211 30/348 |
| 5,275,607 A | 1/1994 | Lo et al. | |
| 5,320,113 A * | 6/1994 | Tan | A61F 9/013 606/1 |
| 5,419,761 A * | 5/1995 | Narayanan | A61B 17/22012 604/22 |
| 5,520,679 A | 5/1996 | Lin | |
| 5,653,724 A | 8/1997 | Imonti | |
| 5,921,999 A * | 7/1999 | Dileo | A61F 9/00745 606/166 |
| 5,957,921 A | 9/1999 | Mirhashemi et al. | |
| 6,083,236 A * | 7/2000 | Feingold | A61F 9/013 606/166 |
| 6,231,582 B1 * | 5/2001 | Gandianco | A61F 9/013 606/166 |
| 6,251,118 B1 * | 6/2001 | Proudfoot | A61F 2/147 606/166 |
| 6,254,619 B1 * | 7/2001 | Garabet | A61F 9/013 606/166 |
| 6,258,053 B1 | 7/2001 | Mackool | |
| 6,514,237 B1 | 2/2003 | Maseda | |
| 6,514,238 B1 | 2/2003 | Hughes | |
| 6,524,251 B2 | 2/2003 | Rabiner et al. | |
| 6,589,201 B1 | 7/2003 | Sussman et al. | |
| 6,592,541 B1 | 7/2003 | Kurwa | |
| 6,830,555 B2 | 12/2004 | Rockley et al. | |
| 6,979,328 B2 | 12/2005 | Baerveldt et al. | |
| 7,153,316 B1 * | 12/2006 | McDonald | A61F 9/0133 606/166 |
| 8,016,843 B2 | 9/2011 | Escaf | |
| 8,052,672 B2 | 11/2011 | Laufer et al. | |
| 8,623,040 B2 | 1/2014 | Artsyukhovich et al. | |
| 8,876,745 B2 | 11/2014 | Escaf | |
| 8,911,460 B2 | 12/2014 | Neurohr et al. | |
| 9,259,234 B2 | 2/2016 | Robertson et al. | |
| 9,278,027 B2 | 3/2016 | Sussman | |
| 9,693,897 B2 | 7/2017 | Vezzu | |
| 10,045,882 B2 | 8/2018 | Balicki et al. | |
| 10,258,505 B2 | 4/2019 | Ovchinnikov | |
| 10,456,321 B2 | 10/2019 | Shadduck | |
| 10,463,536 B2 | 11/2019 | Clauson et al. | |
| 10,463,537 B2 | 11/2019 | Horvath et al. | |
| 10,736,686 B2 | 8/2020 | Rontal et al. | |
| 10,779,991 B2 | 9/2020 | Kahook et al. | |
| 10,842,670 B2 | 11/2020 | Korb et al. | |
| 10,881,551 B2 | 1/2021 | Kraemer et al. | |
| 10,932,951 B2 | 3/2021 | Schaller et al. | |
| 11,241,335 B2 | 2/2022 | Carter et al. | |
| 11,284,957 B2 | 3/2022 | Denlinger et al. | |
| 2002/0055753 A1 * | 5/2002 | Silvestrini | A61F 2/148 606/166 |
| 2002/0111608 A1 | 8/2002 | Baerveldt et al. | |
| 2003/0003418 A1 * | 1/2003 | Kumabe | A61C 1/07 433/119 |
| 2004/0199192 A1 | 10/2004 | Akahoshi | |
| 2004/0260320 A1 * | 12/2004 | Lisk, Jr. | A61F 9/0133 606/166 |
| 2005/0165345 A1 * | 7/2005 | Laufer | A61B 18/1402 604/26 |
| 2006/0041220 A1 * | 2/2006 | Boukhny | A61B 17/320068 606/169 |
| 2007/0060926 A1 | 3/2007 | Escaf | |
| 2007/0265649 A1 * | 11/2007 | Perez | A61F 9/013 606/166 |
| 2008/0234710 A1 | 9/2008 | Neurohr et al. | |
| 2009/0012533 A1 * | 1/2009 | Barbagli | A61B 34/70 606/130 |
| 2011/0106102 A1 | 5/2011 | Balicki et al. | |
| 2011/0196399 A1 * | 8/2011 | Robertson | A61B 17/320783 606/169 |
| 2012/0072197 A1 * | 3/2012 | Ovchinnikov | A61F 9/00745 703/11 |
| 2015/0216725 A1 | 8/2015 | Korb et al. | |
| 2015/0272781 A1 * | 10/2015 | Vezzu | A61F 9/00745 606/169 |
| 2016/0354245 A1 | 12/2016 | Horvath et al. | |
| 2017/0007452 A1 | 1/2017 | Depenbusch | |
| 2017/0056636 A1 * | 3/2017 | Shadduck | A61H 9/0057 |
| 2017/0128122 A1 | 5/2017 | Rontal et al. | |
| 2017/0246036 A1 | 8/2017 | Kraemer et al. | |
| 2019/0183681 A1 * | 6/2019 | Schaller | A61F 9/00781 |
| 2019/0269557 A1 | 9/2019 | Clauson et al. | |
| 2020/0069468 A1 * | 3/2020 | Litherland | A61F 7/00 |
| 2020/0107961 A1 | 4/2020 | Kahook et al. | |
| 2020/0178998 A1 * | 6/2020 | Behzadi | A61F 2/4609 |
| 2020/0289230 A1 * | 9/2020 | Denlinger | A61B 90/361 |
| 2020/0289319 A1 | 9/2020 | Carter et al. | |

OTHER PUBLICATIONS

Wikipedia contributors, "Small Incision", The Free Encyclopedia, Wikipedia, retrieved from tttps://en.wikipedia.org/wiki/Small_incision_lenticule_extraction on Oct. 13, 2021.
TI, DRV2605 ERM and LRA Haptic Driver Evaluation Kit, User's Guide SLOU389A, Revised 2014, 36 pgs., Texas Instrument Inc., retrieved on Feb. 24, 2022 from https://www.ti.com/lit/ug/slou389a/slou389a.pdf.

* cited by examiner

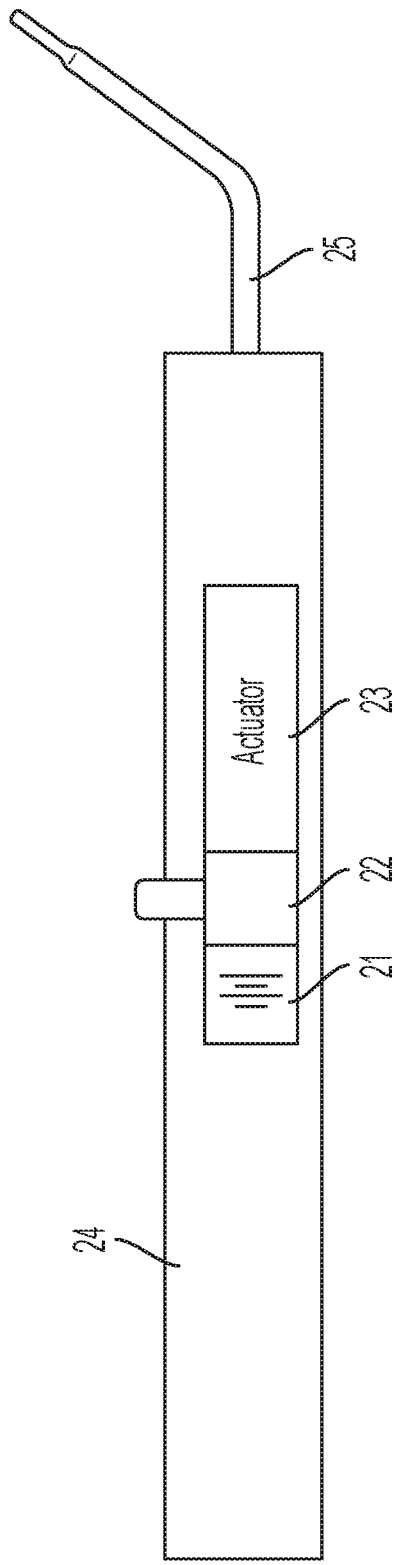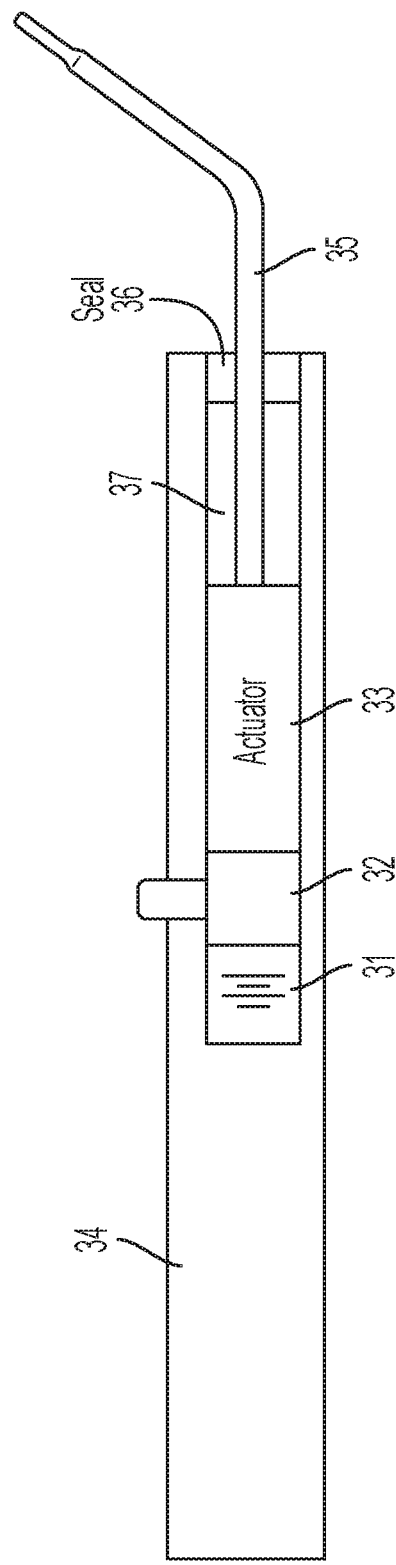

VIBRATING SURGICAL INSTRUMENT

BACKGROUND OF THE INVENTION

The invention relates to a surgical instrument and more particularly a vibrating tissue separator.

DESCRIPTION OF THE RELATED TECHNOLOGY

Refractive eye surgery is used to improve the refractive state of the eye and decrease or eliminate dependency on glasses or contact lenses. This can include various methods of surgical remodeling of the cornea (keratomileusis), lens implantation or lens replacement. Refractive eye surgeries are used to treat common vision disorders such as myopia, hyperopia, presbyopia and astigmatism.

In 1930, a Japanese ophthalmologist, Tsutomu Sato, attempted to perform refractive surgery by making radial cuts in the cornea, correcting effects by up to 6 diopters. The procedure produced a high rate of corneal degeneration, however, and was soon rejected by the medical community.

Jose Barraquer developed a refractive surgery technique in 1963 called keratomileusis, meaning corneal reshaping, enabled correction of myopia and hyperopia. Keratomileusis involves removing a corneal layer, freezing it so that it could be manually sculpted into the required shape, and reimplanting the reshaped layer into the eye.

Another procedure, radial keratotomy (RK) involves making a number of cuts in the cornea to change its shape and correct refractive errors. The incisions are made with a diamond knife. Following the introduction of RK, doctors routinely corrected nearsightedness, farsightedness, and astigmatism using various applications of incisions on the cornea.

In 1980, Rangaswamy Srinivasan, a scientist at IBM found that an excimer could be used to cut organic tissues with high accuracy without significant thermal damage. The discovery of an effective biological cutting laser, along with the development of computers to control it, enabled the development of new refractive surgery techniques. Photorefractive Keratectomy (PRK), or keratomileusis in situ (without separation of corneal layer) was an early laser vision correction technique to reshape the cornea. In PRK surface cells, called epithelial cells are removed and the curvature of the cornea is then modified by applying a laser treatment to its surface. The corrected curvature of the cornea then allows light to come into focus accurately within the eye. Another photorefractive surgical technique called LASIK surgery involves cutting a flap in the cornea and pulling it back to expose the corneal bed, then using an excimer laser to ablate the exposed surface to the desired shape, and then replacing the flap.

LASIK and PRK were broad-beam techniques. Several enhancements have improved certain aspects of refractive surgery. U.S. Pat. No. 5,520,679, the disclosure of which is expressly incorporated by reference herein, disclosed a scanning laser (or flying spot laser) thought to be safer and able to be constructed at a lower cost, more compact, and perform more precisely and with greater flexibility than prior laser systems using the theory of beam overlap and of ablation rate and coagulation patterns for system parameters. According to U.S. Pat. No. 5,520,679, scanning lasers are selected with energy of 0.01-10 mJ, repetition rate of 1-10,000 pulses/second, pulse duration of 0.01 nanoseconds to a few hundreds of microseconds, and with spot size of 0.05-2 mm for use with refractive laser surgery. The scanning laser system patent described various lasers which have been used for refractive surgeries and that the then existing ophthalmic lasers had a "high-power requirement in UV lasers for photorefractive keratectomy; large size and weight; high maintenance cost and gas cost (for excimer laser), and high fiber-cost for contact-type laser coagulation."

Another enhancement for refractive surgery is the use of an eye-tracking device to prevent decentration in LASIK procedures. The idea is to compensate for eye-movements made during a laser refractive eye surgery such LASIK.

In a LASIK procedure Excimer laser ablation is done under a partial-thickness lamellar corneal flap. The surgeon uses either a microkeratome or a femtosecond laser to cut a flap of the corneal tissue. The flap is lifted like a hinged door. A microkeratome is a precision surgical instrument with an oscillating blade designed for creating the corneal flap.

Femtosecond lasers have numerous advantages over mechanical microkeratome based procedure. Microkeratome related flap complications like incomplete flaps, buttonholes or epithelial erosion are eliminated with femtosecond laser procedure. Absence of microscopic metal fragments from the blade will reduce the risk of lamellar keratitis also. When a femtosecond laser flap is created in LASIK (the same femtosecond laser as used in the SMILE procedure used) with the same settings, the LASIK flap easily separates, even with a very blunt instrument such as a 25-gauge cannula.

Another refractive procedure is SMall Incision Lenticule Extraction (SMILE), originally called Femtosecond lenticule extraction (FLEx), is a form of laser based refractive eye surgery developed by Carl Zeiss Meditec used to correct myopia, and astigmatism. Although similar to LASIK laser surgery, the intrastromal procedure shown in the SMILE is novel in that it uses a single femtosecond laser referenced to the corneal surface to cleave a thin lenticule from the corneal stroma for manual extraction. It has been described as a painless procedure. For candidates to qualify for this treatment, they have their corneal stroma thickness checked to make sure that post-operative thickness won't be too thin.

The lenticule to be extracted is accurately cut to the correction prescription required by the patient using a photo disruption laser-tissue interaction. The method of extraction can be via a LASIK-type flap, but more recently a flapless technique makes a small tunnel incision in the corneal periphery.

The femtosecond laser does not completely separate the lenticule, a blunt spatula or a specially designed instrument is inserted through the incision to separate and remove the lenticule through the incision. Care must be taken to ensure that the lenticule is completely detached prior to removal by forceps. The procedure is minimally invasive compared with flap based treatments and collateral damage to surrounding tissue is minimized due to the high speed of the femtosecond laser.

A surgeon performing femtosecond laser created lenticule removal must develop the skill to remove the lenticule without causing trauma or damage to the stromal tissue.

Sinha, Ranesh, et al., *Ophthalmic Surgical Instruments*, Jaypee Brothers Medical Publishers Ltd., 2017, is expressly incorporated by reference herein and shows various instruments which are used in ophthalmic surgery.

SUMMARY OF THE INVENTION

An object is to provide a surgical instrument that may be used to separate tissue without damage to surrounding tissues.

It is a further object to provide a vibrating instrument for separating layers, particularly along lines or planes of weakness, such an instrument may be useful for delicate operations where use of manually induced forces alone risks damage to surrounding tissue or materials. Application of vibratory forces may be useful in separating a tooth and surrounding gum tissue. Such an instrument may be helpful in cataract and other ocular surgery procedures such as to open primary and secondary femtosecond laser created corneal incisions in femtosecond laser assisted cataract surgery and in other procedures to raise a flap in femtosecond LASIK and release adhesions under the flap; to aid in the proper placement of an Implantable Collamer Lens (ICL); and an Intacts corneal separator.

It is a further object to provide an instrument that has a vibrating frequency far below ultrasonic frequencies. Vibration frequencies are set to exceed manually applicable frequencies but not so high as to create a risk of damage. For example, it is an object to provide a device for use in ocular surgery that is not designed to modify refractive error or refractive properties of corneal tissue, in particular, to be more effective and safer than manual separation but not intended to have a different resulting structure than manual separation.

It is a further object to provide a vibrating instrument to assist in separating a lenticule formed by application of a femtosecond laser or by a photodisruption laser-tissue interaction.

According to an advantageous feature a vibrating tissue separator may include a handle sized as a handheld surgical instrument. An actuator may be mounted in the handle and a surgical implement may be mechanically linked to the handle. A control circuit may be connected to the actuator and a power source may be connected to the control circuit. The surgical implement and the actuator may be fixed to the handle, or the surgical implement may be slideably mounted in a channel in the handle.

A seal may be present in the channel between the implement and the handle. A damping element between the handle and the actuator may be provided and the actuator may be slideably mounted in a channel in the handle. The actuator may be an LRA. The damping element may be a spring, a shock absorber, or a block of elastomer.

The control circuit may be a switch. The control circuit may include a feedback controller configured to increase power output in proportion to resistance in movement of the actuator. The control circuit may be a haptic driver having closed loop frequency control.

The directional components of the vibratory movement may be adjusted using a vibrational translator. The vibrational translator may be a hinge in the surgical implement located between a proximal portion of the surgical implement and a distal portion of the surgical implement where the distal portion of the surgical implement exhibits a bend. The hinge may be a bell crank. Another implementation of the vibrational translator may be by having the actuator connected to a pivot mount, where pivoting the mount will change the direction of linear vibration of an LRA. The pivot mount may be a bell crank or, may be a pivot to set the angle of radial vibration around a pivot axis extending along the length of a handle.

The surgical implement may have a tip in the form of a semi-sharp spatula, a blunt spatula, a round blunted wire, a loop, or other shape according to preference of a surgeon.

It is an object to provide a vibrating surgical tool, such as a vibrating blunt spatula which may be used for to separate tissue. The cornea is a flexible, relatively inelastic, clear structure made of five layers. The layer that is treated with refractive surgery is the stromal layer which has an orientation of many fine horizontal lamellae. Historically, lamellar corneal transplants were performed by using a semi-sharp spatula to separate these layers manually. In the SMILE procedure, the desired layers are partially pre-cut with the femtosecond laser allowing a similar handheld instrument to complete the tissue dissection.

While SMILE has many properties making it more desirable to a patient than other refractive procedures, such as less tissue being cut and a single laser used which is not subject to some of the variables which can result in excimer laser variability, SMILE is technically more difficult to perform.

In a SMILE procedure, a femtosecond laser makes many spots close together, but not touching in a spiral pattern. First the deeper layer is cut with a curvature to match the desired refractive error change in sphere and cylinder. Internal side cuts may then be made by the femtosecond laser which establishes a 30 micron edge to a lenticule. Then an upper layer is cut which is parallel to the corneal surface, very similar to a flap. A small opening is created to allow a blunt spatula or other instrument to be introduced to complete the tissue dissection first of the upper and then the lower layer, after which the tissue may be removed with a forceps. The resulting tissue, or lenticule, is very thin. Typically, the resulting lenticule is approximately 30 microns on the edge and varying to between 30 and 120 microns thick in the center, with a diameter of approximately 6.0-7.0 mm.

The laser used in SMILE does not fully cut the tissue for several reasons. One is that the spots, even if touching are round and there will still be an uncut region between spots since they cannot overlap. The second is that there would be a very long time to complete the procedure, which has risks of the patient moving among others. The third is that the amount of energy delivered to the eye would be much higher and have potential risks related to heat and other effects. In practice, the spots are 1 micron in diameter and usually spaced 4.5 microns apart. The femtosecond laser works by creating very short duration high pulse energy spots that result in a plasma and a surrounding shock wave. It is this shock wave that cuts or weakens the surrounding tissue. This effect is variable from patient to patient and to some extent from laser to laser. Therefore, the perforations created by the laser spots are not consistent across patients and thus, the difficulty of separating the lenticule is not consistent between patients.

The disclosed vibrating surgical tissue separator solves the problem of separating the lenticule. As is known, movement of a blade increases its effective sharpness or cutting action. This is one possible modality that can be accomplished by a vibration assistance to the semi-sharp spatula. There are two other modes of effect possible: i) a pushing/chopping motion and ii) a lifting motion. The vibrating instrument may apply a combination of the three modes, set by a surgeon, to assist in separating structures, such as a lenticule created in a SMILE procedure.

It is an advantageous feature to provide an instrument which may apply a vibration imparting a motion having a significant lifting component. It has not been reported that a lifting motion may enhance the ease of lenticule separation. A conventional spatula cannot apply an effective lifting motion due to the structure of the cornea and spatial imitations. In traditional femtolasik, once the perimeter of the flap has been cut, insertion of a cannula or blunt spatula in the pre-cut tissue plane a primarily lifting with slight pushing motion easily separates the flap. In SMILE, there is no peripheral circumferential cut, and the only entrance to the surgical area is through a small 30 to 45 degree opening. Therefore, while it is possible to both push and move from side to side the conventional spatula, in the enclosed space, it is not possible to provide any lifting force. The cornea has a high young's modulus, it does not stretch very much so after just a small amount of lifting, in an enclosed restricted space, the lifting is limited. With vibration in a lifting direction at a relatively high frequency, the separation by lifting is enabled.

In the design of this device, by changing the angle of the spatula from where its attachment exits the device to the tip, a varying combination of pushing (the motion if the wire is straight to the spatula) to lifting (if the wire is bent 90 degrees towards the end) is accomplished. The relative amounts of lifting and chopping depends on the angle of the surgical implement. The lifting with vibration is very small amplitude of a fraction of a millimeter but at a relatively high frequency of hundreds of times per second, which cannot be accomplished manually. Thus the pushing and lifting are automated, and the surgeon can swing the cannula side to side to accomplish some cutting motion as well. The cutting motion is the most dangerous to continuing the separation beyond the desired pre-cut location, and therefore automation should be minimized in the design.

An ERM motor which vibrates by an eccentric rotating motor shaft which vibrates at approximately 8000 Hz or higher may be used, but this configuration appears to be at a higher frequency than needed. Furthermore, it is implemented with a DC motor with a DC source and, thus may be difficult to control due to it being controlled only by varying the voltage applied, which limits control of the amplitude and frequency as well as direction of the vibrations.

Advantageously an LRA motor that runs on AC voltage, and has a frequency the same as the AC sine or square wave fed to them may be used. Using either a signal generator, such as an H-Bridge, or a microprocessor or other integrated circuit specialized for delivering AC pulses from a DC source allows for control of frequency, pulse pattern, and other desirable pulse characteristics. The frequency for these LRA devices as utilized in prototypes is in the range of 200-300 Hz which seems adequate for the intended purposes. An LRA has vibration primarily along one axis (Z axis) which can be aligned in the desired direction of movement, and there are microprocessors allowing for smart control of LRA's which are helpful. For example, a Dialog Semiconductor DA7282 LRA/ERM Ultra-Low Power Haptic Driver with Multiple Input triggers and Integrated Waveform Memory, shown in Dialog Semiconductor DA7282 Datasheet Revision 3.0 30 Jul. 2019 CFR0011-120-00, expressly incorporated by reference herein, may be used to drive the LRA and impart a cyclic vibration of increasing and decreasing amplitude over time, can be tuned to the exact resonance of the device, and can be modulated based on the resistance to vibration with increasing the current and or voltage to maintain a given frequency. The resistance to vibration may be determined by sensing the phase between current through and voltage applied to the LRA. In addition, the frequency as well as the amplitude of the vibration may be controlled by changing primarily the sine wave frequency delivered and/or the voltage delivered to the device.

There is also the possibility of using two LRA devices in series to increase or modulate the effect between them. When run in phase the amount of vibration is the sum of each individually, and when out of phase they can cancel out the effect. LRA's also have the advantage of extremely low latency and provide therefore the desired effect without any delay from the input programming.

The driver may compensate for the difficulty that a surgeon may encounter manually adjusting the operation of the LRA while conducting delicate eye surgery. The driver may automatically vary the intensity of vibration. The device can auto adjust the impedance to correct for varying amounts of resistance during the procedure, thus making it a "smart device" where the surgeon advances the tip and the amount of vibration will vary from a baseline level depending on the amount of resistance encountered. There is also the capability to give tactile feedback to the surgeon with a series of short haptic sensations. These can be used to indicate activation of the device or changing conditions and after it is removed from the eye that it has been turned off.

A device may be approximately 100 mm long, not including the tip, which will be designed to resemble the conventional tip on a manual all metal surgical instrument and be approximately 8.5 mm in widest diameter with tapering at either end. This will be approximately the size that a surgeon is familiar with for such a standard surgical instrument. There may be an on/off switch or a film that can be pulled for activation with haptic feedback of operational self-check and ready status. The device may be single packaged as sterile and disposable. One device can be used for both eyes and then discarded. The body/handle may be made of plastic with internal batteries, controller chips, LRA motor, spring, and insulation from vibration with a small, sealed hole in the front from which the treatment wire protrudes and then bends to the functional spatula tip.

A hinge, such as a Bell Crank hinge may be used in the instrument to translate movement in one direction to another. The angle of the surgical implement may be adjusted at the hinge. A non-hinge option to adjust motion direction is to change the orientation of the LRA motor to accommodate the desired motion or alternatively use an ERM motor which vibrates in multiple directions.

While the vibrating tissue separator is suited for eye surgery, a similar type of situation occurs in other fields such as dentistry, orthopedic surgery, neuro-surgery, or any field where tissue must be separated from another tissue plane from within a restricted space and thus similar tools to this one would have applicability in these other medical disciplines.

The surgical implements used in the vibrating instruments may include blunt spatula, semi-sharp spatula, and other implements that will have enhanced performance when vibrations are imparted to such implement, including separators, hooks, wires, loops, and those shown in Sinha, Ranesh, et al., *Ophthalmic Surgical Instruments*, Jaypee Brothers Medical Publishers Ltd., 2017.

Various objects, features, aspects, and advantages of the present invention will become more apparent from the following detailed description of preferred embodiments of the invention, along with the accompanying drawings in which like numerals represent like components.

Moreover, the above objects and advantages of the invention are illustrative, and not exhaustive, of those that can be achieved by the invention. Thus, these and other objects and advantages of the invention will be apparent from the description herein, both as embodied herein and as modified in view of any variations which will be apparent to those skilled in the art.

BRIEF DESCRIPTION OF THE DRAWINGS

FIG. 2 shows vibrating surgical instrument with a fixed actuator and fixed surgical implement.

FIG. 3 shows an embodiment with of the vibrating tissue separator with a reduced translation of vibratory forces to the handle.

DETAILED DESCRIPTION OF THE PREFERRED EMBODIMENT

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range is encompassed within the disclosed subject matter.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Figure 1:
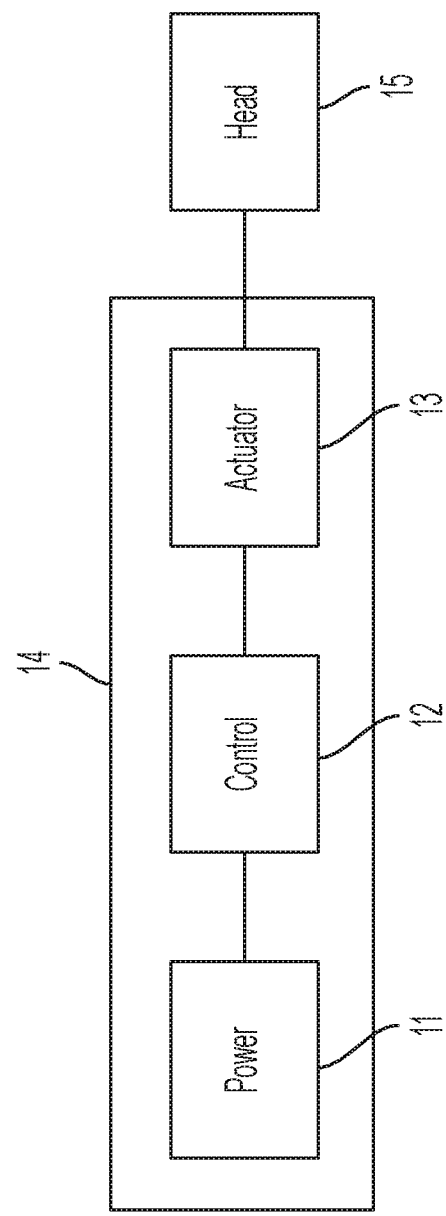
FIG. 1 shows a schematic diagram of a surgical instrument.

FIG. 1 shows a schematic diagram of a surgical instrument, in particular a tissue separator. The instrument may rely on a blunt tip or blade useful to separate tissue, such as along a plane created by a femtosecond laser. For example, a corneal incision, flap or a lenticule created by a laser in a SMILE procedure. The instrument may also be useful to separate material along any line, plane, or area of weakness. The blunt tip may be a spatula to avoid using a sharp instrument which could damage surrounding tissue, particularly if misapplied. The use of a blunt instrument can reduce the incidence of accidentally cutting tissue which should remain intact. The use of a blunt instrument, such as a spatula, however, has been found to be difficult to manipulate and difficult to use to separate tissues such as a lenticule as created during a SMILE refractive technique. The femtosecond laser system achieves the best results when the laser is not set to completely separate the lenticule from the remaining corneal tissue. The treatment parameters of the laser are typically set to achieve enhanced visual results and not for ease of separation of the lenticule. It has been found that placing very closely spaced spots with the laser which would ease separation of a lenticule may delay visual recovery and does not give the best visual outcome. To avoid the effects of many closely spaced laser spots, a surgeon must complete the dissection of the plane created with the laser and separate and extract the lenticule. The instrument may include a spatula which vibrates preferably, at a frequency below ultrasonic frequencies. The frequency range found to be effective is between 200-500 Hz, but all frequencies in the audible range can be reproduced with LRA devices and therefore frequencies between 20-20,000 Hz may be acceptable. The instrument may be a powered vibratory spatula which may include a power supply 11, for example, a battery connected through a control mechanism 12 to an actuator 13 mounted within a handle 14.

The instrument may be provided with a surgical implement or head 15 as the tissue separating implement. The power source 11 may be matched to the actuator 13. For example, if the actuator requires a DC voltage, the power supply 11 will put out a DC voltage level. Alternatively, and in the preferred embodiment, if the actuator requires an AC voltage, the power source 11 may be arranged to provide an AC voltage. A control circuit 12 may be provided to allow a surgeon to apply power to the actuator 13 and disconnect power from the actuator 13. The control circuit 12 may be a switch or may be more involved in order to regulate voltage levels provided to the actuator 13. The head 15 having a surgical implement, such as a blunt spatula, may be arranged to vibrate by application of vibratory energy generated by the actuator 13.

An actuator is a device that produces motion by converting energy and signals going into the system. The motion it produces may be either rotary or linear. Linear actuators, as the name implies, produce linear motion, and can move forward or backward on a set linear plane. Linear actuators typically travel a set distance in either direction. Rotary actuators on the other hand produce rotary motion. Haptic actuators are available which are suitable to the vibratory instrument. A linear resonant actuator (LRA) and an eccentric rotating mass (ERM) motor are common haptic actuators which may be used in the surgical instrument. Haptic actuators and haptic drivers are well known and widely available, albeit not for the current application. See, for example, Texas Instruments, *SLOU 389A—May 2014—Revised June* 2014, *User's Guide, DRV2605L ERM and LRA Haptic Driver Evaluation Kit*, retrieved Oct. 14, 2021, and Dialog Semiconductor, *DA7282, LRA/ERM, Ultra-Low Multiple Input Triggers and Integrated Waveforth Memory, CFR* 00011-120-0, *Datasheet Revision* 3.0, 30 *Jul.* 2019, the disclosures of both are hereby expressly incorporated by reference herein. The driver may be controlled by a microcontroller, for example, a PIC18F06/16Q41, 14/20 Pin, Low-Power, High Performance Microcontroller with XLP Technology, available from Microchip Technology Inc. and described in Datasheet DS4002214E, the disclosure of which is expressly incorporated by reference herein. There are many other commercially available microcontrollers suitable to this application.

FIG. 2 shows a vibrating surgical instrument with a fixed actuator 23 and fixed surgical implement 25. The instrument shown in FIG. 2 includes a power supply 21 connected through a control such as a switch 22 and an actuator 23 or other activation mechanism. The control is illustrated as a switch. However, it should be recognized that the control may include a microcontroller and a haptic driver of the type discussed above. The switch may include a button which extends through the surface of a handle 24. When a surgeon depresses or slides the switch 22 power is supplied to the actuator 23 causing a vibration in the instrument handle 24. The vibration is translated to a head 25 fixed to the handle 24. The embodiment shown in FIG. 2 has the advantage of simplicity in design and construction, however, a user may find that the amount of vibration translated through the handle 24 reduces tactile sensation needed for microsurgery. This is more expected in the ERM type vibrators. In the LRA vibrators, it is easier to isolate the vibration to only the tip 25 with less transmission through the handle 24. It may also be awkward to manually activate the device repeatedly. Therefore, smart control where the device is activated at a low level but can increase the vibration due to impedance may be preferred. As a matter of preference, translation of the vibration however may provide a direct indication of the operation of the actuator to the user. The switch may remain on when released or be a switch that requires contact to remain on.

FIG. 3 shows an embodiment of a vibrating tissue separator with a reduced translation of vibratory forces to the handle 34. The instrument shown in FIG. 3 includes a power supply 31 connected through a control such as a switch 32 and an actuator 33. The switch 32 may include a button which extends through the surface of a handle 34. When a surgeon depresses or slides the switch 32, power is supplied to the actuator 33 causing a vibration in the instrument handle. The vibration is translated to a head 35. As shown in FIG. 3, the actuator may be mounted within a channel 37 of the handle so that motion is imparted to the surgical implement 35 which extends through the channel 37. According to the embodiment of FIG. 3, the surgical implement 35 is not rigidly linked to the handle 34. For example, the surgical implement 35 extending through the channel 37 maybe smaller than the channel. A seal 36 may be provided between the surgical implement 35 and the handle 34 to prevent penetration of liquids and other contaminants into the surgical instrument. The seal will facilitate sterilization of the instrument. The seal 36 may be silicone or other appropriate material which will withstand an autoclave sterilization process without losing its integrity or flexibility. In addition, the seal 36 may provide a damping effect to the head 35.

Figure 4:
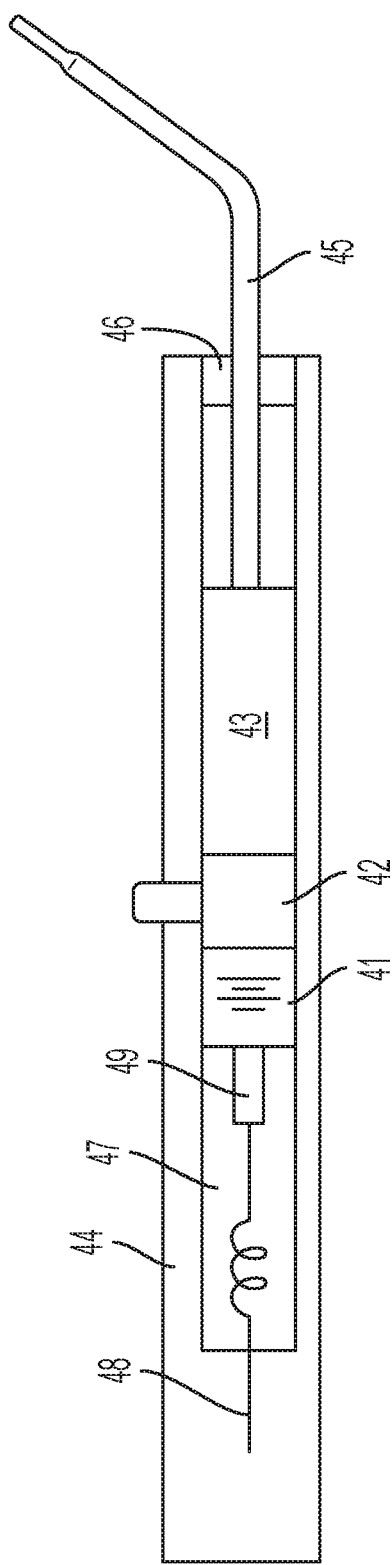
FIG. 4 shows an embodiment of the tissue separator which includes further damping structures for reducing translation of vibrational forces to the handle.

FIG. 4 shows an embodiment of the tissue separator which includes further damping structures for reducing translation of vibrational forces to the handle 44. The instrument shown in FIG. 4 includes a power supply 41 connected through a control such as a switch 42 and an actuator 43. The switch may include a button which extends through the surface of a handle 44. When a surgeon depresses or slides the switch 42, power is supplied to the actuator 43 causing a vibration in the instrument handle. The vibration is translated to a head 45. As shown in FIG. 4, the actuator may be mounted within a channel 47 of the handle 44 so that motion is imparted to the surgical implement 45 which extends out of the channel 47. According to the embodiment of FIG. 4, the surgical implement 45 is not rigidly linked to the handle 44. For example, the surgical implement 45 extending through the channel 47 may be smaller than the opening of the channel 47 at the end of the handle 44. The opening of the 44 and the portion of the surgical implement 45 extending through the opening of the channel 44 may respectively be sized to allow the surgical implement 45 to slide in the channel 47. A seal 46 may be provided between the surgical implement 45 and the handle 44 at the opening of the channel 47 to prevent penetration of liquids and other contaminants into the surgical instrument. The seal will facilitate sterilization of the instrument. The seal may be silicone or other appropriate material which will withstand an autoclave sterilization process without losing its integrity or flexibility. The embodiment according to FIG. 4 has an actuator 43 that is not rigidly attached to the handle 44. A vibrational damping element 48 is shown schematically as a spring, may be added to the surgical instrument. The damping element 48 is provided to further isolate the actuator 43 from the handle 44. Other elastomeric structures may be provided to isolate the handle 44 from a linking element 49 and other intermediate elements to the surgical implement 45. One end of the damping element 48 may be fixed relative to the handle 44 while the other end is fixed to a linking element 49 (and relative to the surgical implement 45). In this configuration, the linking element 49 is mechanically isolated from the handle structure 44. For example, a spring may be mounted in a cylinder installed in a channel 47 of the handle 44. One end of the spring may be fixed to the base of the channel (part of the handle) and the other end of the spring may be fixed to a linking element 49 such as a piston. The linking element 49 may extend through the channel 47 and connected to a battery 41 which is connected to a mechanical switch 42 and then to an actuator 43. The battery 41, mechanical switch 42, an actuator 43 may be all contained in the channel of the handle, but not rigidly fixed to the handle structure itself. The surgical implement 45 may be connected to the actuator 43 but not fixed to the handle 44.

Figure 4A:
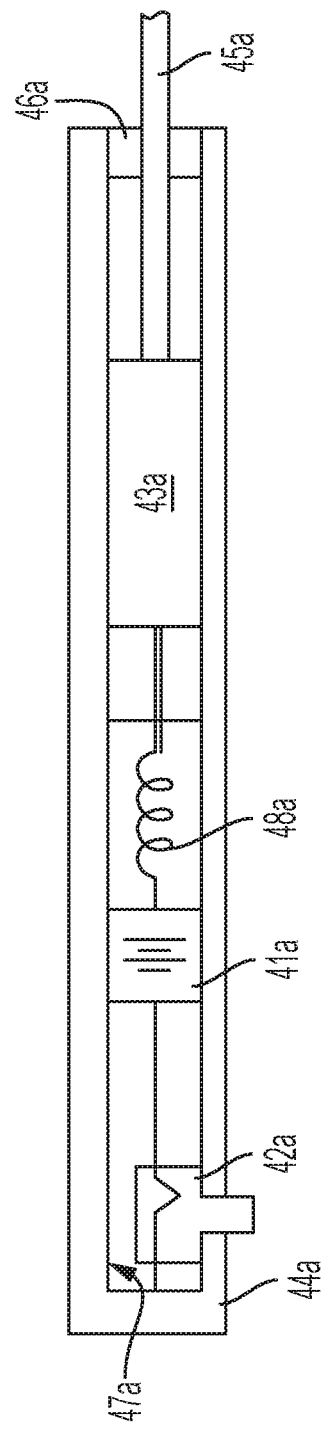
FIG. 4A, shows an alternative implementation of the instrument illustrated in FIG. 4.

FIG. 4a, shows an alternative implementation of the instrument illustrated in FIG. 4, but with the switch 42a and battery 41a being mounted in the handle 44a along with one end of the damping element 48a. The linking element 49a and actuator 43a are not rigidly fixed to the handle and may move within the channel 47a.

Figure 4B:
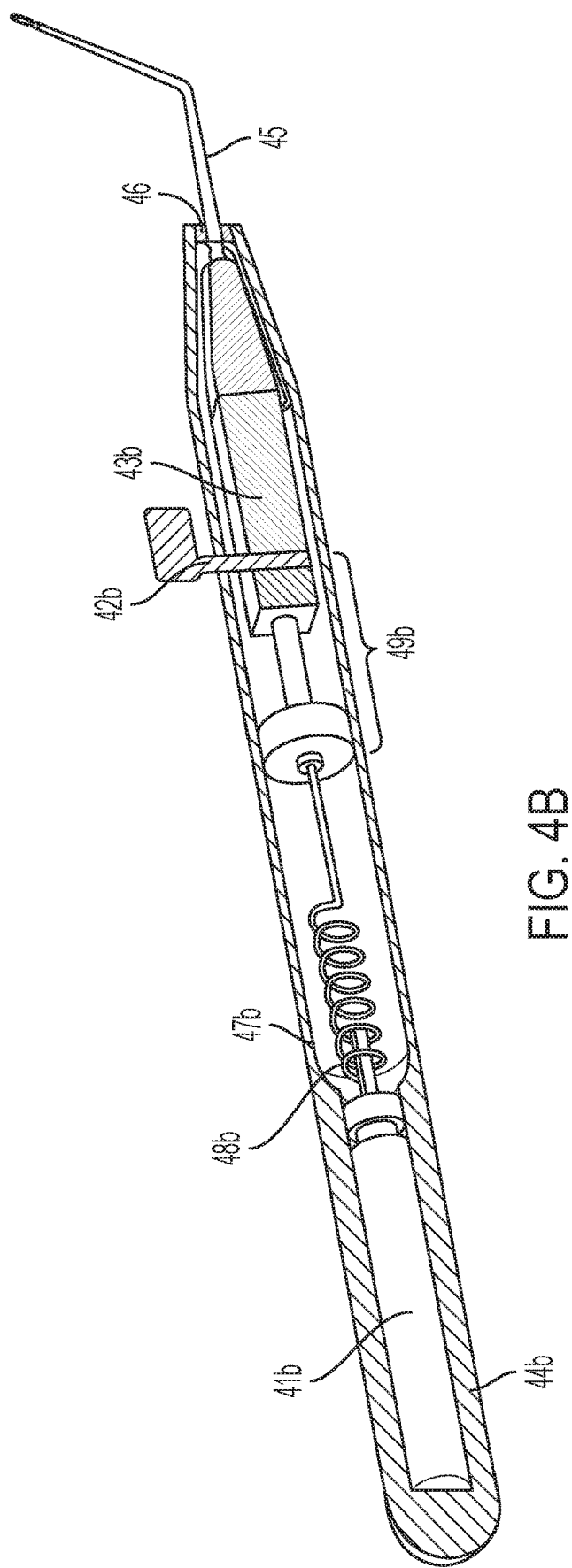
FIG. 4B, shows a further alternative implementation of the instrument illustrated in FIG. 4.

FIG. 4b, shows a further alternative implementation of the instrument illustrated in FIG. 4, but with the battery 41b being rigidly mounted in the handle 44b along with one end of the damping element 48b. The linking element 49b and actuator 43b are not rigidly fixed to the handle and may slide or move within the channel 47b. The switch 42b is shown only schematically as the mechanical and electrical structure are not intended as limitations switch 42b may represent control and activation circuitry as described hereafter.

Figure 5:
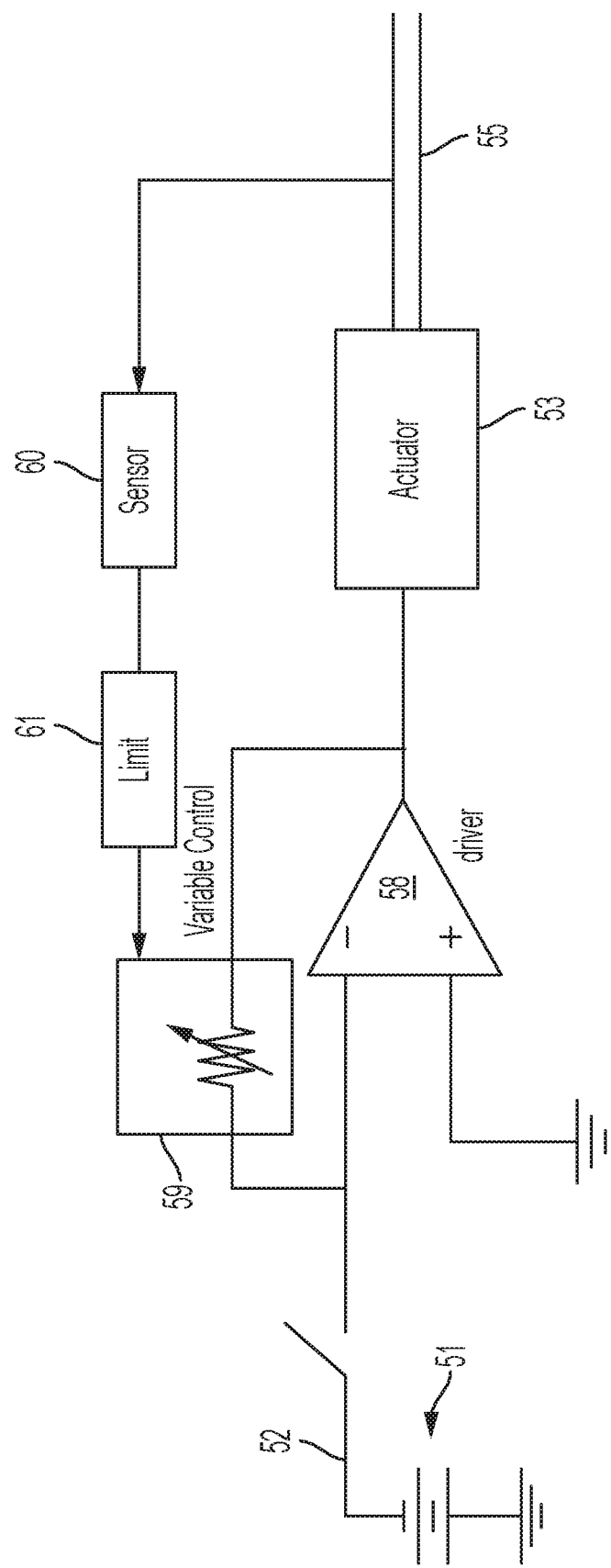
FIG. 5 shows a schematic of an actuator control circuit.

FIG. 5 shows a schematic of an actuator control circuit. The control circuit according to FIG. 5 allows resistance encountered by the surgical implement to control the magnitude of the operation of the actuator. The control circuit according to FIG. 5 is designed so that, optionally, to a limit, the forces created by the surgical implement will increase the magnitude and/or frequency of vibration. The resistance based variable control permits an operation of the instrument where a low level of vibration is generally utilized for tissue separation, however, if resistance to the forces applied to the surgical implement increase, the magnitude of vibration excursion can be increased to compensate for the resistance encountered. An increase in "resistance" may be sensed by detection of a reduction in the frequency of the vibration. The feedback circuit may then increase the current and or voltage to maintain the desired frequency of vibration. FIG. 5 shows a power supply 51 connected through an actuating switch 52. The driver 58 may be provided to apply a control voltage level to the actuator 53. The voltage control may be applied through a feedback channel. A sensor 60 is provided to detect vibration of the implement. For example, when resistance is encountered, the level of vibration may be decreased through the encountered resistance. A sensor 60 may be provided to detect changes in the operation parameters of the surgical instrument 55. The sensors may be conditioned through certain limits. For example, the limits may provide for a base vibration level when no force is applied to the surgical implement. The sensor may be arranged to detect the level of motion imparted to the surgical implement. As the resistance increases, the motion will decrease. This decrease motion may be detected by sensor 60 to a variable control in the driver feedback loop 59. When resistance increases, motion will decrease and amplification will increase. The limit 61 may be provided to control adjustments of the variable control 59 so as to contain the vibration level. In addition, the vibration level may be limited to a set amount no matter how much force. In addition, the limit may operate to provide a minimal vibratory force when the instrument is actuated.

In an actual implementation the control circuit of FIG. 5, may be implemented using a micro-controller, such as the Microchip PIC18F06 and a Haptic Driver chip such as the Dialog Semiconductor DA7282. The resistance encountered by the implement may be sensed and the actuator may be controlled using internal feedback and monitoring by the haptic driver chip or by the microcontroller monitoring the status information made available by the Haptic Driver. As described in the DA7282 Datasheet, the DA7282 is a haptic driver that features frequency control within an onboard Waveform Memory and three distinct GPI inputs, for triggering up to six distinct sequences. The device controls the level of drive across the load and senses the movement of the actuator. The driven waveform is generated by a current regulated loop using a high-frequency PWM modulation. The differential output drive features a switching regulator architecture with H-bridge differential drive across the load. The drive level is based on the sequence from the data source selected by I2C interface, input PWM signal, or Waveform Memory. DA7282 is capable of closed-loop actuator monitoring while driving to enable calibration-free playback, frequency tracking (LRA only), Active Acceleration, Rapid Stop, and actuator diagnostics. Continuous resonant frequency tracking can be enabled while driving an LRA to track the mechanical resonance of the actuator through closed-loop control.

Figure 6:
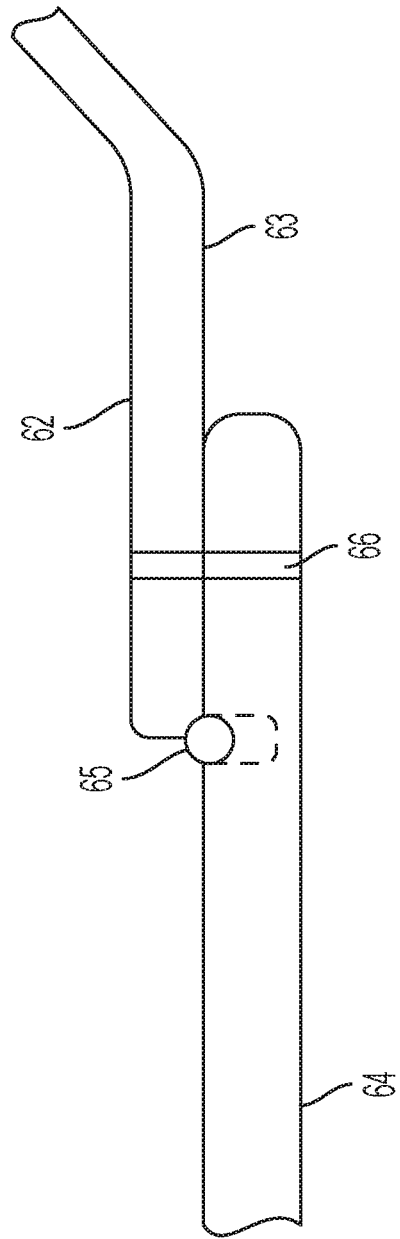
FIG. 6 shows a side view of a vibrational translator for use in a vibrating tissue separator.
Figure 7:
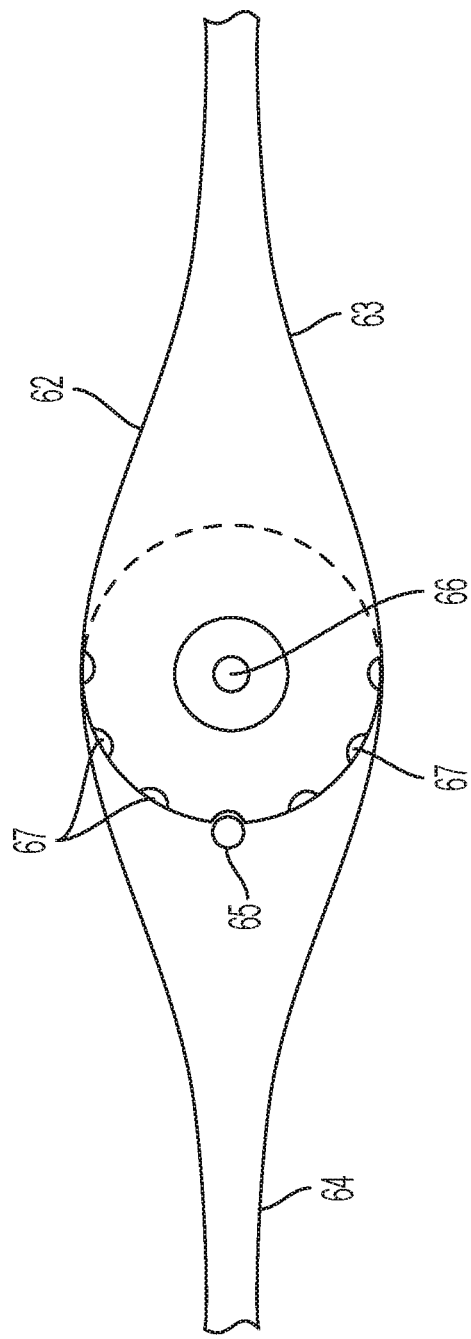
FIG. 7 shows a top view of a vibrational translator for use in a vibrating tissue separator.

FIGS. 6 and 7 show a vibrational translator 61 for use in a surgical instrument such as a vibrating tissue separator. FIG. 6 shows a side view of the vibrational translator 62. FIG. 7 shows a side view of the vibrational translator 62. The vibrational translator 62 may be used with any of the foregoing embodiments in order to adjust the direction of movement of the surgical implement 25, 35, 45, 45a, and 45b and may be placed in the intermediate portion of the proximal segment of the surgical implement. Depending on the particular application, a surgeon may wish the instrument to impart a lifting motion, i.e. perpendicular to a flattened face of the surgical implement, a slicing motion, i.e. parallel to a line defined by leading edge of the surgical implement, or a pushing motion, i.e. perpendicular to a line defined by the leading edge of the surgical edge or any combination thereof. The translation of the motion may be established using a vibrational translator. One implementation is in the form of a hinge which allows rotation of an angled distal end 63 of a surgical implement relative to an implement arm 64 at the proximal end of the surgical implement extending from a handle (not shown) where the implement arm may be connected to a vibrating mechanism, for example as shown in FIGS. 2, 3, 4, 4a, and 4b. Rotation of the hinge, such as a bell crank between the distal end 63 and the proximal end 64 of the surgical implement has the effect of changing the direction of vibration at the distal end. The proximal end 64 of the implement arm may carry a releasable locking mechanism 65 such as a spring loaded bearing or other resilient protrusion. The angled surgical implement, distal arm 63 may be connected to the proximal end 64 of the implement arm by a pivot hinge 66. The distal end 63 (angled) of the surgical implement may have indents 67 distributed around a perimeter of the end of the angled surgical implement 62 that is pivot mounted to implement arm 63. The indents 67 are sized and positioned to cooperate with the releasable locking mechanism 65. In this way, the surgeon may set the rotational position of the distal end 63 of the angled surgical implement to translate the vibrational direction of the implement to set the relative amounts of a lifting, chopping and slicing component of its vibration.

Alternatively the orientation of the LRA device could be modified to change the orientation of the "Z" axis of the LRA resulting in a change in the direction of vibration at the distal end of the surgical implement. This may be accomplished by rotating an actuator mounted on or attached to a bell crank so as to provide oscillation about the pivot of the crank. Adjusting the orientation of the crank changes the direction of vibration, and thus motion of the implement, to alter the relative components of slicing, chopping and lifting motions.

The electrical connections (not shown) for the embodiments shown in FIGS. 2, 3, 4, 4a, 4, b and 6 are provided so as to accommodate vibrations induced by the actuator and relative movement of the mechanical elements. The electrical connections may include slide contacts which maintain continuity even in the event of relative motion. The controllers (not shown in FIGS. 2, 3, 4, 4a, 4, b and 6) may include a switch or other surgeon activated control, a driver, such as a Dialog Semiconductor DA7282 Haptic Driver and a power supply controller.

Figure 8:
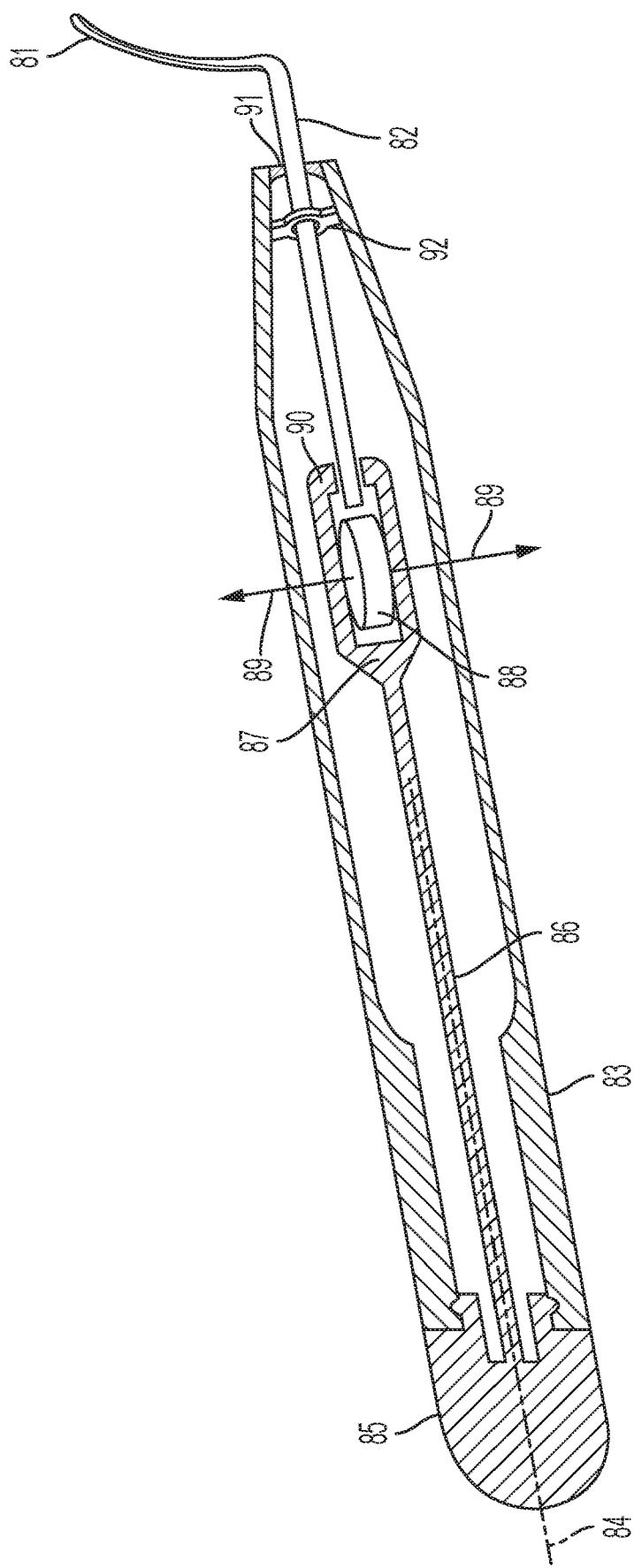
FIG. 8 shows an alternative implementation with a radially vibrating LRA.

FIG. 8 shows a further alternative implementation of a vibrating surgical instrument. A surgical implement 81 is arranged at the distal end of implement arm 82. Implement arm 82 extends from the instrument handle 83. The instrument handle 83 has a central axis 84. End cap 85 is rotationally attached to the handle 83 and is provided to twist around the axis 84 of the handle 83. A haptic driver, microcontroller, switch, and power source may be arranged in a recess not shown in the twisting end cap 85. An actuator arm 86 may extend from the end cap 85 through the hollow center of the handle 83. The distal end 87 of the actuator arm 86 is configured to hold LRA 88. LRA 88 when activated vibrates in the directions shown by arrows 89. The distal tip 90 of the actuator arm is configured to engage implement arm 82 in order to move the implement arm 82 in the direction of vibrations 89, but is not fixed to implement arm 82 so that the actuator arm 86 may be rotated without rotating the implement arm 82. Implement arm 82 may be connected to the handle 83 by an elastomeric resilient seal 91 at the distal end of the handle. In addition, the implement arm 82 may extend through a collar 92 which operates to relieve vibrational stresses on the seal 91 and which acts as a pivot point allowing seal 91 to act as a damping mechanism due to its elastomeric qualities. The conductor supplying electrical power may be arranged through or on the actuator arm 86. The end cap 85 may be rotated about the axis 84 to change the radial direction of vibration 89. The implement arm 82 is rotationally fixed to the handle 83. The rotational alignment of the end cap 84 and the actuator 89 when set to be perpendicular to the face of the surgical implement tip 81 will impart a combination of pushing movement and lifting movement to the implement tip 81. By rotating the end cap 85 90° the radial direction of vibration of the LRA 88 is also changed by 90° degrees. Changing the direction of vibration in this fashion will eliminate the lifting and pushing motion of the implement tip 81 and instead impart a slicing motion.

The simplified version of the tissue separator shown in FIG. 8 may be provided, which does not permit changing the vibration direction of the implement head. In the simplified embodiment, the collar 92 may be replaced by a pivot point and the end cap 85 may be rigidly connected to the handle body 88 thereby eliminating rotation of the end cap 85, rotation of the actuator arm 86, and fixing the direction of vibration of the LRA 88.

The techniques, processes and apparatus described may be utilized to control operation of any device and conserve use of resources based on conditions detected or applicable to the device.

The invention is described in detail with respect to preferred embodiments, and it will now be apparent from the foregoing to those skilled in the art that changes and modifications may be made without departing from the invention in its broader aspects, and the invention, therefore, as defined in the claims, is intended to cover all such changes and modifications that fall within the true spirit of the invention.

Thus, specific apparatus for and methods of use have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A surgical hand instrument for separating tissue layers comprising:
   a handle sized as a handheld surgical instrument for freehand use;
   a vibrating actuator mounted in said handle;
   a surgical implement linked to said vibrating actuator, said surgical implement exhibiting a tip suitable for separating tissue layers, wherein said surgical implement has a generally planar tip;
   a control circuit connected to said actuator;
   wherein said vibrating actuator is linked to said surgical implement to impart vibration to said tip and wherein said vibration includes a lifting component, wherein said lifting component is perpendicular to a plane defined by said generally planar tip and wherein said lifting component of said vibration has a frequency of 200 Hz to 500 Hz; and
   a power source connected to said control circuit.

2. The surgical hand instrument for separating tissue layers according to claim 1 wherein said surgical implement is fixed to said handle and said actuator is fixed to said handle.

3. The surgical hand instrument for separating tissue layers according to claim 1 wherein said surgical implement is slidably mounted in a channel in said handle.

4. The surgical hand instrument for separating tissue layers according to claim 3 further comprising a seal in said channel between said surgical implement and said handle.

5. The surgical hand instrument for separating tissue layers according to claim 3 further comprising a damping element between said handle and said actuator and wherein said actuator is slideably mounted in said channel in said handle.

6. The surgical hand instrument for separating tissue layers according to claim 5 wherein said actuator is a linear resonant actuator (LRA).

7. The surgical hand instrument for separating tissue layers according to claim 5 wherein said damping element is a spring, a shock absorber, or a block of elastomer.

8. The surgical hand instrument for separating tissue layers according to claim 7 wherein said control circuit comprises a switch.

9. The surgical hand instrument for separating tissue layers according to claim 8 wherein said control circuit further comprises a feedback controller configured to increase power output in proportion to resistance in movement of said actuator.

10. The surgical hand instrument for separating tissue layers according to claim 9 wherein said control circuit further comprises a haptic driver having closed loop frequency control.

11. The surgical hand instrument for separating tissue layers according to claim 5 further comprising a second damping element arranged to interact with said surgical implement and provide a damping effect to said surgical implement.

12. The surgical hand instrument for separating tissue layers according to claim 3 further comprising a vibrational translator, wherein said vibrational translator is a bend in said surgical implement located between said generally planar tip and a proximal portion of said surgical implement.

13. The surgical hand instrument for separating tissue layers according to claim 12 wherein said bend in said surgical implement is provided by a hinge in said surgical implement located between said proximal portion of said surgical implement and a distal portion of said surgical implement.

14. The surgical hand instrument for separating tissue layers according to claim 12 wherein said vibrational translator further comprises a pivot mount and said actuator is connected to said pivot mount.

15. The surgical hand instrument for separating tissue layers according to claim 3 wherein said tip of said surgical implement further comprises a semi-sharp spatula.

16. The surgical hand instrument for separating tissue layers according to claim 3 wherein said tip of said surgical implement further comprises a blunt spatula.

17. The surgical hand instrument for separating tissue layers according to claim 3 wherein said surgical implement further comprises a round blunted wire.

18. The surgical hand instrument for separating tissue layers according to claim 3 wherein said tip of said surgical implement further comprises a loop.

19. A surgical hand instrument tissue separator comprising:
- a handle sized as a handheld surgical hand instrument;
- an actuator mounted in said handle;
- a surgical implement having a generally planar tip, wherein said surgical implement is mechanically linked to said handle and said actuator applies a vibration to said surgical implement wherein said vibration has a lifting component perpendicular to a plane defined by said generally planar tip of said surgical implement and wherein said lifting component has a vibration frequency of 200 Hz to 500 Hz;
- a control circuit connected to said actuator; and
- a power source connected to said control circuit.

20. The surgical hand instrument tissue separator according to claim 19 wherein said tip comprises a blunt spatula.

21. The surgical hand instrument tissue separator according to claim 19 wherein said lifting component has a vibrating frequency in the range of 200 Hz to 300 Hz.

22. The surgical hand instrument tissue separator according to claim 19 further comprising a first damping element between said handle and said actuator and a second damping element arranged to interact with said surgical implement and provide a damping effect to said surgical implement.

* * * * *